United States Patent
Bonneau

(10) Patent No.: US 9,937,318 B2
(45) Date of Patent: Apr. 10, 2018

(54) SAFE URINARY CATHETER AND MANUFACTURING METHOD

(71) Applicant: Safe Medical Design, Inc., San Francisco, CA (US)

(72) Inventor: Raymond Arthur Bonneau, San Francisco, CA (US)

(73) Assignee: SAFE MEDICAL DESIGN, INC., San Francisco, CA (US)

( * ) Notice: Subject to any disclaimer, the term of this patent is extended or adjusted under 35 U.S.C. 154(b) by 0 days.

(21) Appl. No.: 15/494,733

(22) Filed: Apr. 24, 2017

(65) Prior Publication Data

US 2017/0291010 A1    Oct. 12, 2017

Related U.S. Application Data

(63) Continuation of application No. 15/484,911, filed on Apr. 11, 2017, now abandoned.
(Continued)

(51) Int. Cl.
*A61M 25/00*    (2006.01)
*A61M 25/10*    (2013.01)
(Continued)

(52) U.S. Cl.
CPC .... *A61M 25/0017* (2013.01); *A61M 25/1011* (2013.01); *A61M 25/1018* (2013.01);
(Continued)

(58) Field of Classification Search
CPC .............. A61M 25/0017; A61M 5/488; A61M 16/209; A61M 25/1018; A61M 25/10184; A61M 25/10185; A61M 25/10186; A61M 25/10187; A61M 25/10188; A61M 25/1002; A61M 2025/1004
See application file for complete search history.

(56) References Cited

U.S. PATENT DOCUMENTS

| 3,543,758 A | 12/1970 | McWhorter |
| 3,543,759 A | 12/1970 | McWhorter |

(Continued)

FOREIGN PATENT DOCUMENTS

DE    3306342    8/1984

OTHER PUBLICATIONS

International Search Report and Written Opinion for PCT/US2017/027033, dated Aug. 2, 2017, 16 pages.

*Primary Examiner* — Adam Marcetich
(74) *Attorney, Agent, or Firm* — Merchant & Gould P.C.

(57) ABSTRACT

A urinary catheter may include a catheter shaft and a connector coupled with the proximal end of the catheter shaft. The connector may have a first arm ending in a fluid outlet configured to allow urine to flow out of the urinary catheter and a second arm with an aperture and ending in an inflation inlet used for introducing inflation fluid into the urinary catheter. The catheter may further include a primary lumen, an inflation lumen, a retention balloon mounted to the catheter shaft proximal to a fluid inlet and over a distal filling hole, and a pilot balloon mounted on the second arm of the connector over the aperture. The pilot balloon inflates at an inflation pressure that is higher than the inflation pressure of the retention balloon and lower than a predetermined pressure threshold.

16 Claims, 8 Drawing Sheets

Related U.S. Application Data

(60) Provisional application No. 62/321,423, filed on Apr. 12, 2016.

(51) Int. Cl.
  *A61M 39/10* (2006.01)
  *A61M 39/24* (2006.01)

(52) U.S. Cl.
  CPC ...... *A61M 25/10187* (2013.11); *A61M 39/10* (2013.01); *A61M 39/24* (2013.01); *A61M 2025/1015* (2013.01); *A61M 2205/32* (2013.01); *A61M 2207/00* (2013.01); *A61M 2210/1096* (2013.01)

(56) References Cited

U.S. PATENT DOCUMENTS

| | | | | |
|---|---|---|---|---|
| 3,642,005 A * | 2/1972 | McGinnis | ........... | A61M 16/044 128/207.15 |
| 3,985,141 A * | 10/1976 | Stanley | ........... | A61M 16/044 128/207.15 |
| 4,142,525 A * | 3/1979 | Binard | ........... | A61B 17/3401 604/121 |
| 4,248,222 A * | 2/1981 | Jaeger | ........... | A61M 16/044 128/207.15 |
| 4,264,312 A | 4/1981 | Cianci | | |
| 4,329,985 A * | 5/1982 | Bonchek | ........... | A61B 17/00 604/185 |
| 4,335,723 A * | 6/1982 | Patel | ........... | A61L 29/041 604/103 |
| 4,552,558 A * | 11/1985 | Muto | ........... | A61M 16/04 116/DIG. 8 |
| 4,856,510 A * | 8/1989 | Kowalewski | ........... | A61M 16/044 128/207.14 |
| 6,530,898 B1 * | 3/2003 | Nimkar | ........... | A61M 16/044 604/100.01 |
| 6,979,313 B1 * | 12/2005 | Meek | ........... | A61M 25/0017 604/98.01 |
| 9,084,868 B2 | 7/2015 | Aaronson et al. | | |
| 2003/0088263 A1 * | 5/2003 | Bonnette | ........... | A61M 25/09 606/194 |
| 2008/0033570 A1 | 2/2008 | Blitz et al. | | |
| 2008/0200871 A1 * | 8/2008 | Slater | ........... | A61M 25/0097 604/96.01 |
| 2011/0071506 A1 | 3/2011 | Gardner et al. | | |
| 2011/0082444 A1 * | 4/2011 | Mayback | ........... | A61B 5/205 604/544 |
| 2011/0295236 A1 * | 12/2011 | Gregory | ........... | A61M 3/0295 604/540 |
| 2012/0259313 A1 * | 10/2012 | Krumme | ........... | A61M 5/24 604/506 |
| 2015/0051542 A1 * | 2/2015 | Gregory | ........... | A61M 25/10187 604/97.01 |
| 2015/0112312 A1 * | 4/2015 | Mooney | ........... | A61M 25/0017 604/544 |

\* cited by examiner

SAFE URINARY CATHETER AND MANUFACTURING METHOD

CROSS-REFERENCE TO RELATED APPLICATIONS

This application is a continuation of U.S. patent application Ser. No. 15/484,911, filed Apr. 11, 2017, entitled "Safe Urinary Catheter and Manufacturing Method," which claims the benefit of U.S. Provisional Patent Application No. 62/321,423, filed Apr. 12, 2016, entitled, "Manufacturing a Safe Urinary Catheter." The entireties of each application above are herein incorporated by reference.

TECHNICAL FIELD

This application is related to medical devices and methods. More specifically, this application is related to a safe urinary catheter and a method of manufacturing the catheter.

BACKGROUND

A urinary catheter is generally a thin, flexible tube, inserted into the urethra and advanced into the urinary bladder, in order to drain the bladder in patients who cannot urinate normally. For example, urinary catheters are used during surgery, when a patient is under general anesthesia, in some hospital patients to monitor urinary output, and in awake patients with any of a large number of voiding abnormalities, such as urinary tract obstructions, urinary incontinence, and the like.

Indwelling urinary catheters, designed to remain in place for a longer period of time to drain the bladder, include at least two tubes running in parallel. One of the two tubes is a "drainage tube," with a hole at its distal end and a "drainage port" at its proximal end. Urine flows into the hole at the distal end of the drainage tube and out of the drainage port to void the bladder. The second of the two tubes of an indwelling catheter is an inflation tube, which is in fluid communication with an inflatable balloon (often referred to as a "retention balloon") at or near the distal end of the catheter. The retention balloon is inflated within the urinary bladder to maintain the position of the distal end of the catheter within the bladder. The inflation tube (or "balloon tube") generally terminates proximally at an inflation port (or "balloon port"). The inflation tube typically includes a valve, allowing instillation or removal of liquid into or from the balloon (e.g., via a syringe). The balloon diameter, when inflated, is larger than the urethral diameter, thus preventing the inflated balloon from slipping out of the bladder. Each of the two tubes of the indwelling urinary catheter may terminate either outside the patient's body or inside the body, depending on the specific medical application. For example, in some embodiments, the drainage tube can be linked to a urine collection bag.

Unlike most medical devices, urinary catheters are most commonly placed into and removed from patients by nurses, ancillary medical staff, and patients themselves. Unfortunately, incorrect handling and placement of urinary catheters can result in disastrous consequences, and physicians and non-physicians alike report frequent complications associated with placement and removal of urinary catheters. Indeed, urologists are regularly consulted to manage complications associated with misplacement of urinary catheters. A common complication is damage to the urethra (and extreme pain, if the patient is awake) when the balloon at the tip of the catheter is inflated (accidentally) while it resides in the urethra rather than in the bladder. This occurs when the person placing and inflating the catheter has not inserted it far enough through the urethra. This situation can create significant urethral injury, pain and bleeding, and typically necessitates a costly consultation by a surgical specialist. The catheter can usually be replaced after the injury, but may require invasive cystoscopy (placement of a small camera into the urethra). Invariably, in this situation, the catheter must remain indwelling for a longer than intended time period, to allow the urethra to heal and/or to provide pressure to halt the bleeding. Other consequences of intraurethral balloon inflation are urinary tract obstruction, urinary tract infections, discomfort, renal failure, and death. The urethral injury may also result in urethral stricture or narrowing, which can necessitate additional costly surgical interventions.

Another common complication associated with urinary catheters occurs when the catheter balloon bursts inside the patient's bladder. Balloon burst may occur for a variety of reasons, most commonly overfilling of the balloon or device malfunction (e.g., defective balloon). After balloon burst in the bladder, the catheter slides out of the urethra and must be replaced. More significantly, studies have shown that upon bursting, a fragment of the balloon wall frequently breaks away from the shaft of the catheter and remains within the bladder. The balloon fragment must be retrieved, e.g., by a surgical specialist with the aid of a cystoscope. If the fragment is not removed, the patient may have severe urinary symptoms, such as recurrent urinary tract infections and stone formation, which require further medical intervention and expense.

Another common failure of urinary catheters is a balloon that will not deflate. Current recommendations for managing a non-deflating balloon include percutaneous or endoscopic balloon puncture, instillation of chemicals to dissolve the balloon, or over-inflating the balloon to burst it. These techniques, while necessary, can result in balloon fragmentation, patient discomfort, bleeding, and damage to nearby organs.

Yet another complication occurs when a patient or healthcare professional attempts to remove the catheter, or the catheter is accidentally pulled out, while the balloon is still partially or completely inflated. For example the patient or healthcare professional might believe the balloon is deflated when it actually is not, the catheter tubing may snag on another object and get yanked out, a patient with altered mental status may pull out the inflated catheter, etc. The result of pulling out an inflated catheter is similar to that of inflating the balloon within the urethra, but typically more severe, because it may damage the entire length of the urethra. Further complicating premature catheter removal is the necessity to replace the catheter through an already damaged urethra, and possible disruption in some cases of a still healing surgical repair (i.e., after removal of the prostate for cancer or repair of a urethral stricture).

Based on these issues and complications with urinary catheters, it would be very desirable to have catheters that are safer to use and that have a lower likelihood of complications due to misuse or malfunction of the balloon on the catheter. Ideally, such catheters would also be relatively easy to place and inflate, so that a wide variety of healthcare professionals, staff and even patients could use them with little or no additional training.

SUMMARY

The present disclosure describes a urinary catheter with improved safety features, a method for making the urinary catheter, and a method for using the catheter. The catheter and the methods for manufacturing and using it are described in terms of a number of different embodiments, none of which are intended to limit the scope of the disclosure.

In one aspect of the disclosure, a urinary catheter may include an elongate, flexible, tubular catheter shaft having a proximal end and a distal end and a connector coupled with the proximal end of the catheter shaft. The connector may have a first arm ending in a fluid outlet configured to allow urine to flow out of the urinary catheter and a second arm with an aperture and ending in an inflation inlet used for introducing inflation fluid into the urinary catheter. The catheter may also include a primary lumen extending through the catheter shaft from a fluid inlet at or near the distal end of the catheter shaft to the first arm of the connector, an inflation lumen extending through the catheter shaft from a distal filling hole in the catheter shaft to the second arm of connector, a retention balloon mounted to the catheter shaft proximal to the fluid inlet and over the distal filling hole and a pilot balloon mounted on the second arm of the connector over the aperture. The retention balloon is configured to inflate at a first inflation pressure, and the pilot balloon is configured to inflate at a second inflation pressure that is higher than the first inflation pressure and lower than a predetermined pressure threshold.

In various embodiments, the aperture in the second arm of the connector may be one hole, multiple holes, a slit, a gap between two portions of the second arm or the like. In some embodiments, a cross-sectional area of the aperture in the second arm of the connector may be less than a cross-sectional area of the distal filling hole. In some embodiments, the catheter may further include a check valve attached to a proximal end of the second arm, and the inflation inlet may be a proximal end of the check valve.

According to various embodiments, any one or a combination of differences between the retention balloon and the pilot balloon may account for their different inflation pressures. For example, in some embodiments, the retention balloon has a first balloon wall thickness, and the pilot balloon has a second balloon wall thickness that is greater than the first balloon wall thickness. In some embodiments, the retention balloon is made of a first material having a first durometer, and the pilot balloon is made of a second material having a second durometer that is greater than the first durometer. In some embodiments, the retention balloon has a first length, and the pilot balloon has a second length that is different than the first length. In some embodiments, the retention balloon has a first radius, and the pilot balloon has a second radius that is less than the first radius. In some embodiments, the pilot balloon is shaped as a tube, and the retention balloon has a preformed balloon shape, so that a higher pressure is required to begin inflating the pilot balloon than the retention balloon. In some embodiments, the retention balloon has a first inflated shape, and the pilot balloon has a second inflated shape that is different than the first inflated shape.

Optionally, any of the embodiments may include further comprising a radiopaque strip extending through at least a portion of the catheter shaft.

In another aspect of the disclosure, a method of manufacturing a urinary catheter may involve providing an elongate, flexible, tubular catheter shaft having a proximal end, a distal end, a primary lumen extending through the catheter shaft from a fluid inlet at or near the distal end of the catheter shaft to the proximal end of the catheter shaft, and an inflation lumen extending through the catheter shaft from a distal filling hole near the distal end of the catheter shaft to the proximal end of the catheter shaft. The method may also include attaching a connector with the proximal end of the catheter shaft. The connector may include a first arm in fluid communication with the primary lumen and ending in a fluid outlet configured to allow urine to flow out of the urinary catheter and a second arm with an aperture in fluid communication with the inflation lumen and ending in an inflation inlet used for introducing inflation fluid into the urinary catheter. Next, the method may include mounting a retention balloon on the catheter shaft over the distal filling hole and proximal to the fluid inlet and mounting a tubular pilot balloon on the second arm of the connector over the aperture in the second arm. Again, the retention balloon is configured to inflate at a first inflation pressure, and the pilot balloon is configured to inflate at a second inflation pressure that is higher than the first inflation pressure and lower than a predetermined pressure threshold.

Optionally, the method may also include forming the aperture in the second arm. For example, forming the aperture may involve forming at least one of a hole, a slit or a cut in the second arm. In some embodiments, a cross-sectional area of the aperture in the second arm is less than a cross-sectional area of the distal filling hole.

In some embodiments, the method may also include forming the tubular pilot balloon to have a tubular shape and forming the retention balloon to have a preformed balloon shape, such that a higher pressure is required to begin inflating the tubular pilot balloon than the retention balloon. In some embodiments, the method may also include forming the retention balloon to have a first balloon wall thickness and forming the pilot balloon to have a second balloon wall thickness that is greater than the first balloon wall thickness. In some embodiments, the method may also include forming the retention balloon out of a first material having a first durometer and forming the pilot balloon out of a second material having a second durometer that is greater than the first durometer. In some embodiments, the method may also include forming the retention balloon to have a first length and forming the pilot balloon to have a second length that is different than the first length. In some embodiments, the method may also include forming the retention balloon to have a first inflated shape and forming the pilot balloon to have a second inflated shape that is different than the first inflated shape.

In yet another aspect of the disclosure, a method of positioning a urinary catheter in a patient may involve: advancing a distal end of the urinary catheter through the patient's urethra; introducing inflation fluid into the urinary catheter to inflate a retention balloon at or near the distal end of the urinary catheter; observing that a pilot balloon at or near a proximal end of the urinary catheter, located outside the patient, has inflated; waiting for at least a predefined amount of time for the pilot balloon to deflate; and if the pilot balloon deflates during the predefined amount of time, then leave the urinary catheter in place within the patient. If the pilot balloon does not deflate during the predefined amount of time, then the method may involve removing the inflation fluid from the urinary catheter and repositioning or removing the urinary catheter.

In some embodiments, the predefined amount of time may be a range of between 3 and 30 seconds. For example, in one embodiment, the predefined amount of time may be ten seconds. In some embodiments, introducing the inflation fluid may involve injecting the inflation fluid with a syringe attached to an inflation port at or near the proximal end of the urinary catheter. In some embodiments, introducing the inflation fluid may involve injecting between 5 cc and 10 cc of the inflation fluid. In some embodiments, the method may further involve visualizing at least the advancing step via a radiographic imaging device and a radiopaque strip or marker on the urinary catheter.

These and other aspects and embodiments will be disclosed in further detail below, in reference to the attached drawing figures.

DETAILED DESCRIPTION

The present application describes an improved urinary catheter with safety features designed to help prevent catheter-related injuries due to improper inflation, improper removal, balloon burst due to over-inflation and/or the like. The application also describes methods for making and using such a catheter. The embodiments include a relief balloon (also called a "pilot balloon") on the proximal portion of the urethral catheter that resides outside the body. The pilot balloon will relieve pressure from the distal balloon, if the latter is inflated within the urethra. The pilot balloon will typically have a filling pressure that is slightly higher than that of the retention balloon. In this way, the pilot balloon fills only when the retention balloon is subject to greater than expected filling pressures. One example of a urinary catheter with a relief balloon is described in U.S. Pat. No. 9,084,868, which is hereby incorporated by reference in its entirety herein.

For the purposes of this application, unless indicated otherwise, the terms "proximal" and "distal" refer to positions relative to outside of a body into which a catheter is inserted. Accordingly, when inserted in a subject (e.g., a human), the proximal end of a catheter is typically outside of the subject's body, and the distal end of the catheter is typically within the body, for example within the bladder. The terms "subject" and "patient" are used synonymously herein and refer to a human or animal subject.

Figure 1A:
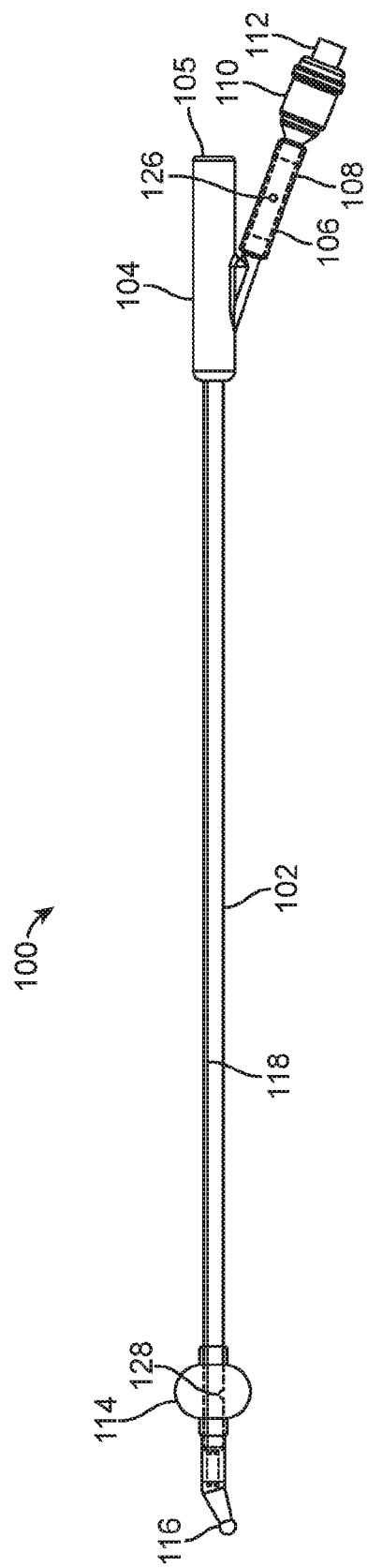
FIG. 1A is a side view of a urinary catheter, according to one embodiment.
Figure 1B:
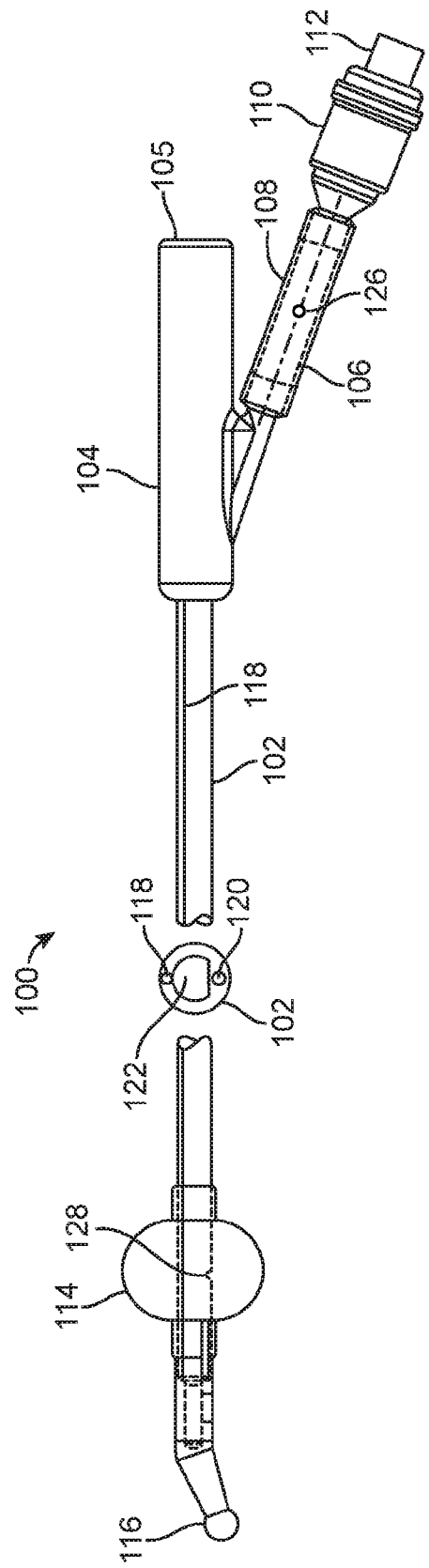
FIG. 1B is a side view of the catheter of FIG. 1A, with a cut-out, cross-sectional view along the length of the catheter shaft.
Figure 1C:
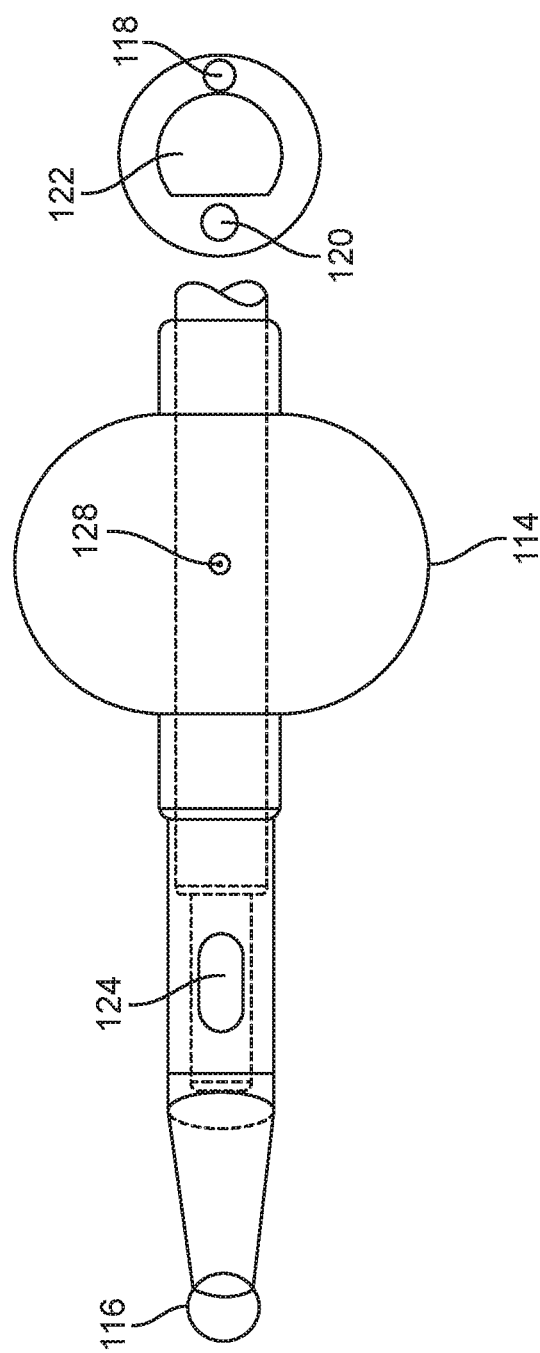
FIG. 1C is a top view of a distal portion of the catheter of FIGS. 1A and 1B.
Figure 1D:
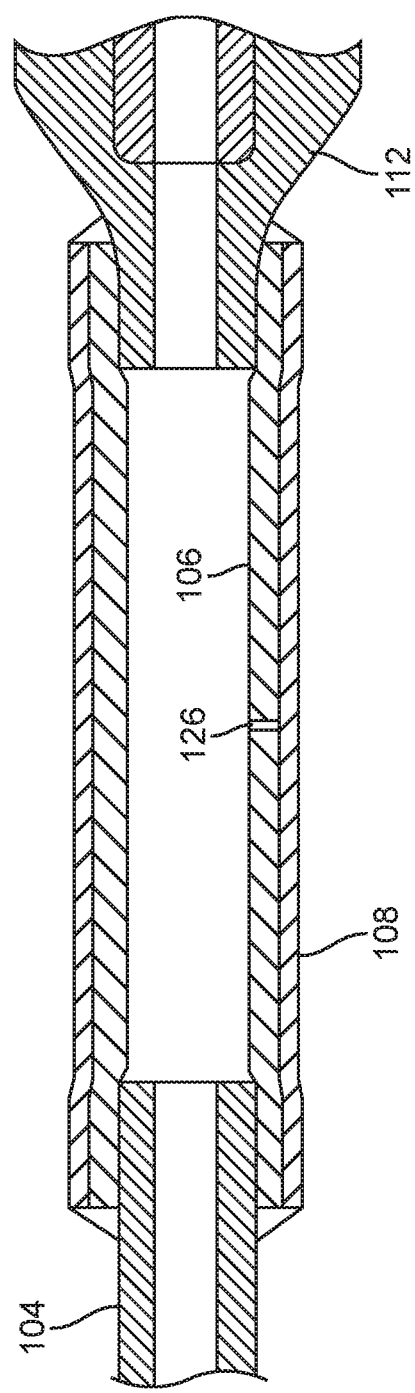
FIG. 1D is a side, cross-sectional view of the pilot balloon portion of the catheter of FIGS. 1A-1C.

Referring to FIGS. 1A-1D, one embodiment of a urinary catheter 100 is illustrated. FIG. 1A is a side view of catheter 100. FIG. 1B is an enlarged, side view of catheter 100 with a section removed from the catheter shaft and with a cross-sectional view of the shaft. FIG. 1C is a top view of a distal portion of catheter 100. FIG. 1D is a side, cross-sectional view of the pilot balloon portion of catheter 100.

In the illustrated embodiment, catheter 100 includes an elongate, flexible, catheter shaft 102 with a rounded distal tip 116, a connector 104 attached to the proximal end of shaft 102, and a retention balloon 114 near the distal end of shaft 102. A first arm of connector 104 ends in a fluid outlet 105, through which urine exits catheter 100. A second arm of connector 104 includes a pilot balloon 108 mounted on a tube 106, and proximal to that a check valve 112 with a sleeve 110. Shaft 102 also includes an inflation lumen 120 (FIGS. 1B and 1C), for inflating retention balloon 114, a primary lumen 122 (or "emptying" or "voiding" lumen), for passage of urine out of the bladder through catheter 100, and a distal hole 124 (FIG. 1C, also called a "fluid inlet"), through which urine enters primary lumen 122 from the bladder. Optionally, shaft 102 may also include a radiopaque strip 118 along all or part of its length, to facilitate radiographic visualization of catheter 100.

Retention balloon 114 is attached to a distal portion of shaft 102, proximal to hole 124. As mentioned above, connector 104 includes fluid outlet 105 (or "urine voiding/emptying end") on one arm and tube 106 attached to the other arm. Tube 106, in turn, is connected to a check valve 112. A pilot balloon 108 is mounted on tube 106, and tube 106 includes one or more apertures 126 (FIG. 1D), through which inflation fluid can flow to inflate pilot balloon 108 if the required inflation pressure is reached inside tube 106. Aperture(s) 126 may be one hole, as shown, multiple holes, a slit, an opening between two sections of tube 106, or any other opening or openings in tube 106. Sleeve 110, which is mounted on check valve 112, may optionally include any suitable labeling, such as but not limited to a size and/or volume label.

As shown in the cross-sectional cut-outs of FIGS. 1B and 1C, inflation lumen 120 may be located within the wall of catheter shaft 102, and primary lumen 122 may be formed by an inner surface of the wall of catheter shaft 102. Alternatively, both lumens 120, 122 may be located within the wall of the catheter in some embodiments. In other embodiments, urinary catheter 100 may include two catheter shafts that run in parallel and are connected, with one shaft forming a primary/emptying lumen and the other shaft forming an inflation lumen.

Referring to FIG. 1D, tube 106 and pilot balloon 108 may be attached at one end to connector 104 and at an opposite end to check valve 112. Any suitable means for attachment may be used, such as but not limited to glue or thermal bonding. In many embodiments, the second arm of connector 104 may simply be a tube branching off of connector 104 and may not include a separate tube 106. In those embodiments, examples of which are pictured in FIG. 4A-5B, aperture 126 (or multiple apertures, a slit, a gap, or the like) are simply located in the second arm of connector 104. As mentioned above, tube 106 may include aperture 126 in some embodiments, as shown, leading from the lumen of tube 106 to an inner surface of pilot balloon 108. If sufficient fluid pressure builds up within tube 106, fluid will exit through aperture 126 and inflate balloon 108. In alternative embodiments, tube 106 may include more than one aperture 126. In other alternative embodiments, other mechanisms in tube 106 may be used. For example, in one embodiment tube 106 may be in two pieces or may include a longitudinal slit, to allow fluid to flow therethrough. In the embodiment illustrated in FIG. 1D, only one aperture 126 is included in tube 106. In one embodiment, the aperture 126 has a diameter of about 1 mm.

In various embodiments, any suitable material or combination of materials may be used to make urinary catheter 100. For example, in some embodiments, catheter 100 may be made completely or primarily out of latex or silicone. In one embodiment, for example, all the components of catheter 100 described above are made of silicone, other than sleeve 110 and check valve 112. For example, sleeve 110 may also be made of silicone, but in one embodiment it is made of acrylonitrile butadiene styrene (ABS). In one embodiment, check valve 112 may also be made of silicone, but alternatively it may be made of silicone or one or more other plastic materials. Radiopaque strip 118 may be made of any suitable, biocompatible radiopaque material.

FIG. 1C, which again is a top view of a distal portion of urinary catheter 100, clearly shows fluid inlet 124 and distal tip 116. Fluid inlet 124 may have any suitable size and shape, for example the ovoid shape pictured here. In one embodiment, fluid inlet is approximately 5.5 mm long and 2.5 mm wide. Distal tip 116 may be a Tiemann or Coude tip, for example. Also visible in FIG. 1C (as well as in FIGS. 1A and 1B) is a retention balloon inflation hole 128, which is in fluid communication with balloon inflation lumen 120 and which allows inflation fluid to flow into retention balloon 114. In one embodiment, retention balloon inflation hole 128 has a diameter of about 1 mm.

In various embodiments, any of the components of urinary catheter 100 may have any of a number of suitable dimensions. Merely by way of example, several dimensions of components have been mentioned above. Also for exemplary purposes only (and not to be considered limiting), additional dimensions of one embodiment of urinary catheter 100 include: 420 mm+/−2 mm from distal tip 116 to fluid outlet 105; length of retention balloon 114 16 mm+/−2 mm; diameter of retention balloon inflation lumen 120 about 1 mm; inner diameter of tube 106 4 mm+/−0.2 mm; length of pilot balloon 31 mm+/−1 mm; outer diameter of pilot balloon 7.6 mm+/−0.2 mm. Again, these are only examples of dimensions for one embodiment of urinary catheter 100 and are not meant to limit the scope of the invention.

In use, distal tip 116 of catheter 100 is advanced through the urethra and into the urinary bladder, and retention balloon 114 is inflated with inflation fluid via an inflation device, such as a syringe (not illustrated) attached to the end of check valve 112. If retention balloon 114 is located in the urethra and not the bladder when the user attempts to inflate it, fluid pressure will quickly build up within tube 106, and pilot balloon 108 will inflate, thus relieving pressure from the retention balloon 114 and alerting the user that retention balloon 114 is not in the bladder. As such, pilot balloon 108 should require a higher threshold opening pressure and/or resting capacity pressure than retention balloon 114. In other words, it should be harder to inflate pilot balloon 108 than retention balloon 114. In various embodiments of urinary catheter 100, for example, pilot balloon 108 has a 15%-75% higher threshold opening pressure and/or resting capacity pressure than retention balloon 114. At the same time, in most embodiments pilot balloon 108 will begin to inflate at a pressure that is below a predetermined threshold pressure that has been designed to enhance safety of urinary catheter 100. In other words, pilot balloon 108 inflates within a predetermined pressure range, with an opening pressure that is higher than that of retention balloon 114 but below the predetermined threshold pressure.

There are a number of ways to manufacture urinary catheter 100 so that pilot balloon 108 has a desired opening pressure relative to retention balloon 114 (and thus inflates as desired). For example, the material used to make pilot balloon 108 is one important variable. In one embodiment, for example, a higher durometer (harder) material may be used to make pilot balloon 108 than retention balloon 114, thus requiring a higher pressure to inflate pilot balloon 108. In some embodiments, however, much or all of urinary catheter 100, including both pilot balloon 108 and retention balloon 114, is made of silicone of the same durometer. In such embodiments, the material for both balloons 108, 114 is the same, so the material does not create the pressure differential.

Another way to give pilot balloon 108 a higher inflation pressure than that of retention balloon 114 is to make the wall of pilot balloon 108 thicker than the wall of retention balloon 114. As just one, non-limiting example, in one embodiment, pilot balloon 108 may have a wall thickness of 0.8 mm+/−0.05 mm, while retention balloon 114 may have a wall thickness of less than 0.8 mm, for example a common retention balloon thickness is 0.5 mm+/−0.05 mm. The thicker wall of pilot balloon 108 will require more pressure to expand than will the wall of retention balloon 114.

Another way to provide variation in inflation pressures between the two balloons 108, 114 is to give the balloons 108, 114 different sizes and/or shapes. In an ideal balloon, the pressure (P) is equal to 2 times the surface tension divided by the balloon radius (P=2*u/R). The surface tension should be the same between spherical balloons, assuming all properties other than size are equal. Therefore, balloon pressure is inversely proportional to the radius, and a smaller radius balloon shape will require a higher pressure to inflate. In one specific embodiment, retention balloon 114 may be a 5 cc balloon, and pilot balloon 108 may be a 3 cc balloon. For example, in this embodiment, the radius of the 5 cc balloon retention balloon 114 may be about 1.05 cm, and the radius of the 3 cc pilot balloon 108 may be about 0.89 cm. In this case, the smaller pilot balloon 108 will require 18% higher pressure to inflate, based on volume relations.

The shapes of the balloons 108, 114 may also be different. For example, in one embodiment of urinary catheter 100, pilot balloon 108 has a tubular shape when not inflated—in other words, it is not pre-shaped as a balloon. In contrast, retention balloon 114 may be pre-shaped as a balloon, and for example may be folded or pleated when in its resting, uninflated state. Additionally, the balloons 108, 114 may have different inflated shapes as well. For example, one of the balloons 108, 114 may be round when inflated, while the other may have an ovoid, ring-like or other inflated shape.

An initial (or "peak") pressure is required to inflate any balloon. For a standard balloon, the peak pressure is typically 10%-25% higher than its resting pressure—i.e., the static pressure in the balloon once it is inflated to its desired size. For example, this is why, when you inflate a party balloon, you initially need to breathe a little bit harder to get the inflation of the balloon started than you do when you are inflating the balloon the rest of the way. When you inflate a balloon that has an initial, uninflated shape of a cylinder, rather than a balloon with an ovoid or round shape, you need to breathe extra-hard at the beginning. In most embodiments of urinary catheter described herein, pilot balloon 108 is cylindrical. Because pilot balloon 108 does not have an initial or uninflated "balloon shape," the peak pressure for pilot balloon 108 may range from 40-75% higher than its resting pressure. This is important, because it prevents "accidental" or "false" inflation of pilot balloon 108. An example of an accidental inflation would be if a urinary catheter were properly placed in the bladder, and only retention balloon 114 should inflate, but instead pilot balloon 108 also inflates. Such inflation sends a false signal to the user and is important to avoid for proper functionality.

In one embodiment, the resting pressure of pilot balloon 108 is approximately 15% higher than the resting pressure of retention balloon 114 (80-90 Kpa for pilot balloon 108 vs. 70 kpa for retention balloon 114). The threshold for urethral damage/trauma is considered to be around 150 Kpa. In one embodiment, pilot balloon 108 will have a peak pressure (or "predetermined pressure threshold") of less than or about 100 Kpa, so that it will start to inflate at that pressure. A standard existing catheter improperly placed will create pressures in excess of 500 Kpa in the urethra, well above this threshold for damage.

Yet another way to regulate the relative inflation pressures of pilot balloon 108 and retention balloon 114 is to select the size of the inflations holes of the balloons 108, 114 according to desired inflation pressure characteristics. The "inflation hole" of a balloon generally refers to the hole through which the balloon is filled and through which it empties. In some cases, the hole may be a slit or other opening in the shaft or between shafts. In the case of retention balloon 114, the retention balloon filling hole 128 traverses through catheter shaft 102 to connect inflation lumen 120 with the interior of retention balloon 114. In the case of pilot balloon 108, aperture 126 traverses the wall of tube 106 to connect the interior of tube 106 with the interior of pilot balloon 108. The pressure drop across a hole is equal to:

$$\Delta P = 2f\left[\frac{L}{D}\right](pxV^2)$$

where ΔP=change in pressure, f=the Moody friction coefficient, L=length, D=diameter, p=the initial pressure, and V=velocity.

This means that a smaller diameter hole will lead to a larger pressure drop across the hole. Similarly, a filling slit or opening with a smaller cross-sectional area will lead to a larger pressure drop. Therefore, it follows that for a given balloon inflation pressure, a greater fill channel pressure would be required to blow up a balloon with a smaller inflation hole. For example, if retention balloon 114 has retention balloon filling hole 128 with a diameter of about 3 mm, and pilot balloon 108 has aperture 126 with a diameter of about 2 mm, it would require 33% greater channel pressure to inflate pilot balloon 108 than it would to inflate retention balloon 114. In other words, in this exemplary embodiment, pilot balloon would not inflate until the channel pressure was 33% higher than that required to fill the retention balloon.

Another way to regulate balloon inflation pressure is by the angle of entry of the inflation hole into the balloon lumen. Before inflation of pilot balloon 108, for example, the wall of pilot balloon 108 covers inflation aperture 126. If the angle of aperture 126 is flat (in other words, oriented perpendicularly to the wall of pilot balloon 108), then the wall of pilot balloon 108 will completely cover the wall of the aperture 126, and will result in a higher threshold opening pressure. If the face of aperture 126 is oriented at an oblique angle to the wall of pilot balloon 108 (when the balloon is completely empty), such that at rest the face of the aperture 126 is not in complete contact with the balloon wall, then the threshold filling pressure will be slightly lower, because the balloon wall is not directly obstructing the entire opening of aperture 126. The angle of an inflation hole can also affect the emptying of a balloon. For example, when the filled balloon is subject to deforming stress, the balloon wall can obstruct the inflation/emptying hole, effectively increasing the pressure necessary to empty the balloon. This design feature may be applied to pilot balloon 108, retention balloon 114 or both.

Some embodiments use a combination of features to create a desired inflation pressure differential between pilot balloon 108 and retention balloon 114. For example, in one embodiment, pilot balloon 108 and retention balloon 114 of urinary catheter 100 may have the following different characteristics: (1) different wall thickness (0.8 mm for pilot balloon 108 vs. 0.5 mm for retention balloon 114); (2) different durometer (40 shore A for pilot balloon 108 vs. 25 shore A for retention balloon 114); and (3) different resting/uninflated shape (tube shape for pilot balloon 108 vs. pre-shaped balloon shape for retention balloon 114). The above example, of course, is only one of many possible embodiments. For example, in various embodiments, pilot balloon 108 may have a thickness of between about 0.6 mm and about 0.9 mm, or more generally pilot balloon 108 may have a thickness that is about 20% to about 80% greater than retention balloon 114. The durometer of the material of pilot balloon 108 may range from equal to that of retention balloon 114 to as much as about 50% greater than that of retention balloon 114. Another factor, which may be used in addition to or as an alternative to any of the above-listed factors, is that pilot balloon 108 may be longer than retention balloon 114. Again, any suitable combination of the above factors, measurements and characteristics may be used, in various embodiments.

Figure 2:
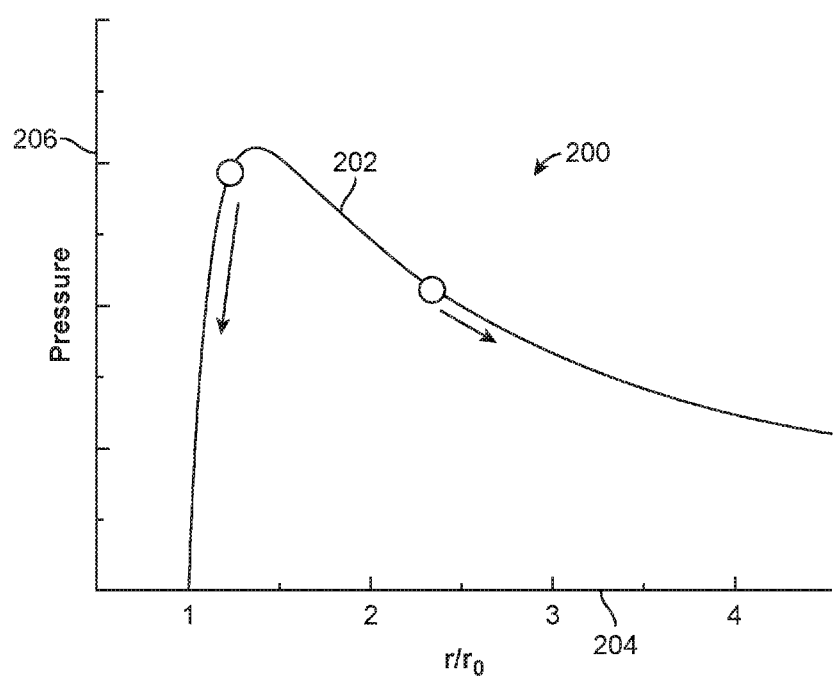
FIG. 2 is a graph showing a radius/pressure curve of an inflating balloon, according to one embodiment.

Referring now to FIG. 2, a graph 200 illustrates a radius/pressure curve 202 for an idealized rubber balloon, according to one example. On graph 200, the x-axis 204 indicates the ratio of the inflated radius to the nominal (uninflated) radius of the balloon, and the y-axis 206 indicates the relative pressure. Curve 202 reveals a way of creating a pressure difference between the two. Pilot balloon 108, for example, could be designed such that it never makes it past the initial peak on the left side of curve 202, while retention balloon 114 is inflated far past this pressure peak, resulting in a lower pressure. In practice, one could achieve this using one or a combination of the above-described methods of varying pressure. Curve 202 also shows that if retention balloon 114 can be inflated past the peak pressure without inflating pilot balloon 108, then pilot balloon 108 should not inflate, unless it is in the wrong location (such as the urethra), and its expansion is being resisted.

Figure 3:
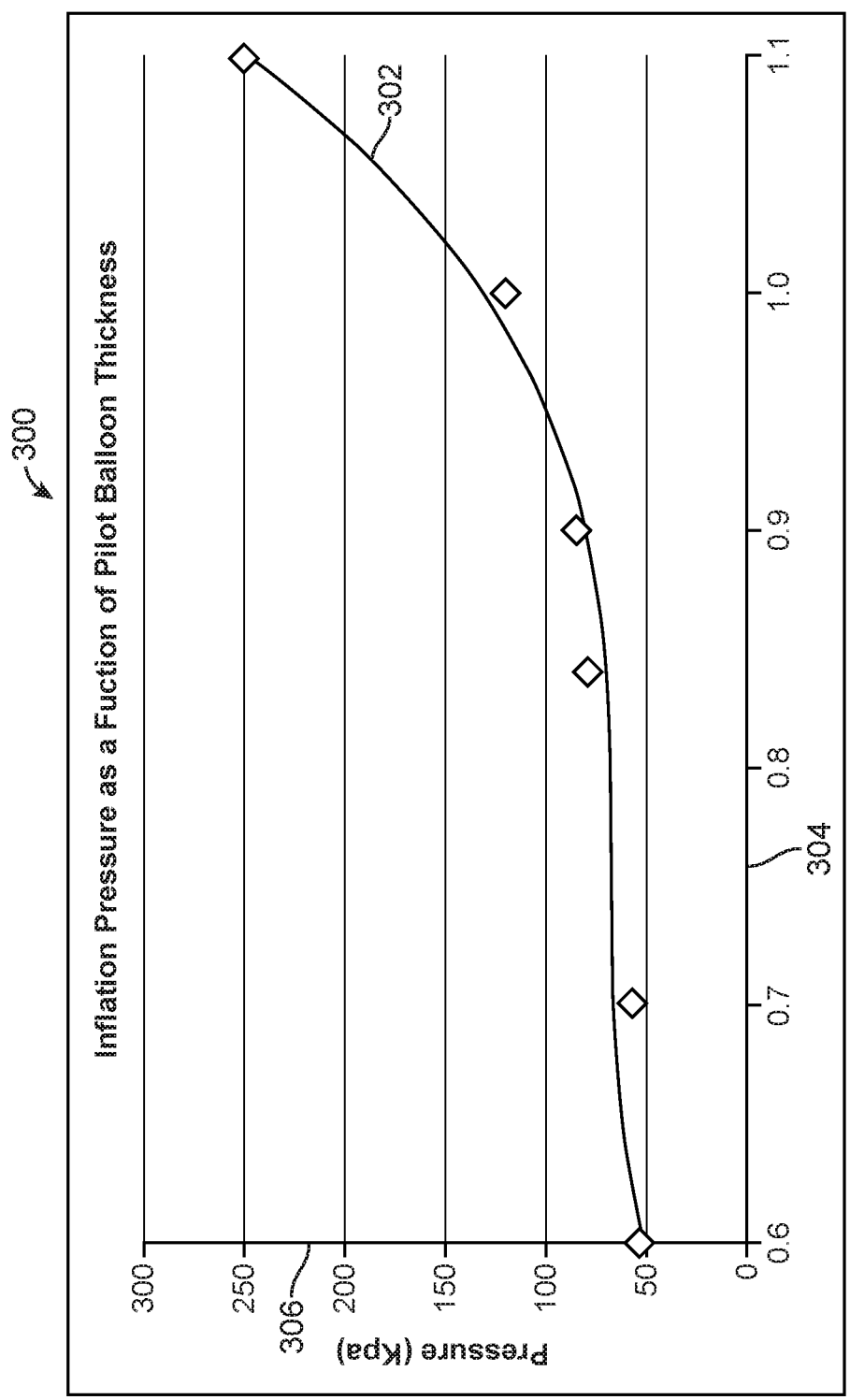
FIG. 3 is a graph showing a balloon wall thickness/pressure curve of an inflating balloon, according to one embodiment.

Referring now to FIG. 3, a graph 300 illustrates a pressure/thickness curve 302 for an idealized rubber balloon, according to one example. On graph 300, the x-axis 304 indicates the wall thickness of the balloon in millimeters, and the y-axis 306 indicates amount of pressure with which the balloon is being inflated. As the balloon increases in wall thickness 304, the pressure to inflate it 306 will rise. The pressure to inflate 306 follows an exponential curve 302. It is therefore important to choose a thickness 304 below the exponential portion of the curve 302, so that slight variations in thickness do not cause a drastic change in the inflation pressure. In some embodiments, for example, the wall thickness 304 of pilot balloon 108 may be selected to achieve a point just before the exponential portion of the curve, to maximize the difference between pilot balloon 108 and retention balloon 114 pressures, while optimizing reliability of pilot balloon 108. In one specific embodiment, for example, pilot balloon 108 may be given a wall thickness of 0.85 mm.

Figure 4A:
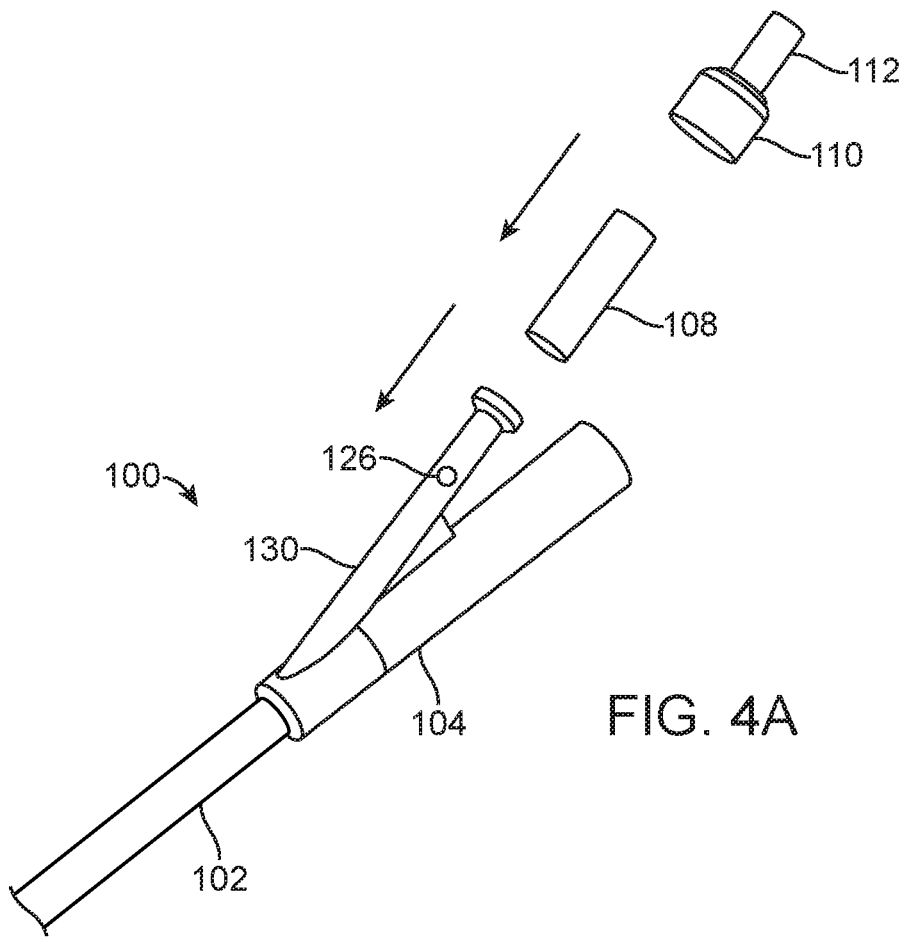
FIGS. 4A and 4B are perspective views of a proximal end of a urinary catheter, illustrating a method for assembling the proximal portion, according to one embodiment.
Figure 4B:
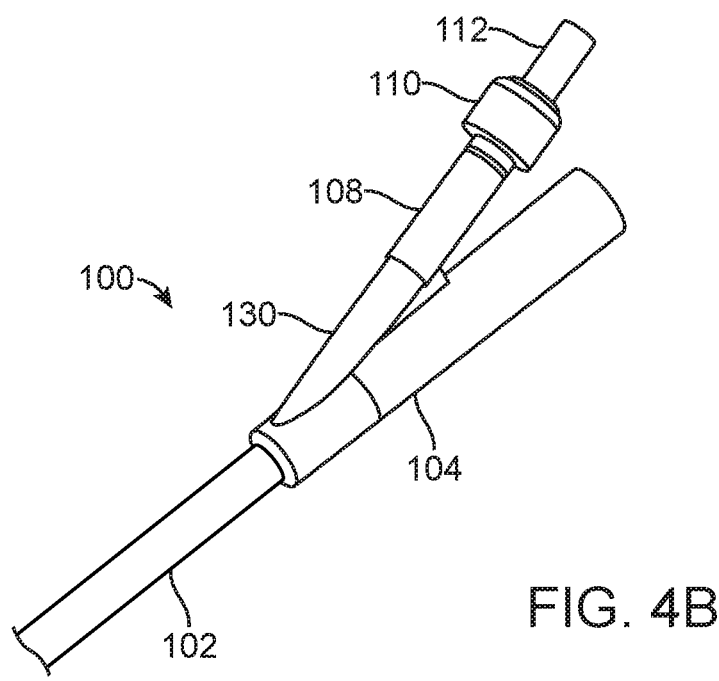

FIGS. 4A and 4B illustrate one method for manufacturing (or "assembling") a portion of urinary catheter 100. In this embodiment, the tube-shaped pilot balloon 108 is mounted directly over the second arm 130 of connector 104, which includes aperture 126 that allows inflation fluid to pass from second arm 130 into pilot balloon 108. Sleeve 110 and check valve 112, which may be a one-piece construction, are then placed over the proximal end of pilot balloon 108. In this embodiment, in other words, second arm 130 acts as tube 106 from previously described embodiments. This is simply an alternative embodiment—e.g., tube 106 may be attached to a proximal end of a second arm in some embodiments, while alternatively second arm 130 may be one piece, without a separate tube 106 attached to it.

Figure 5A:
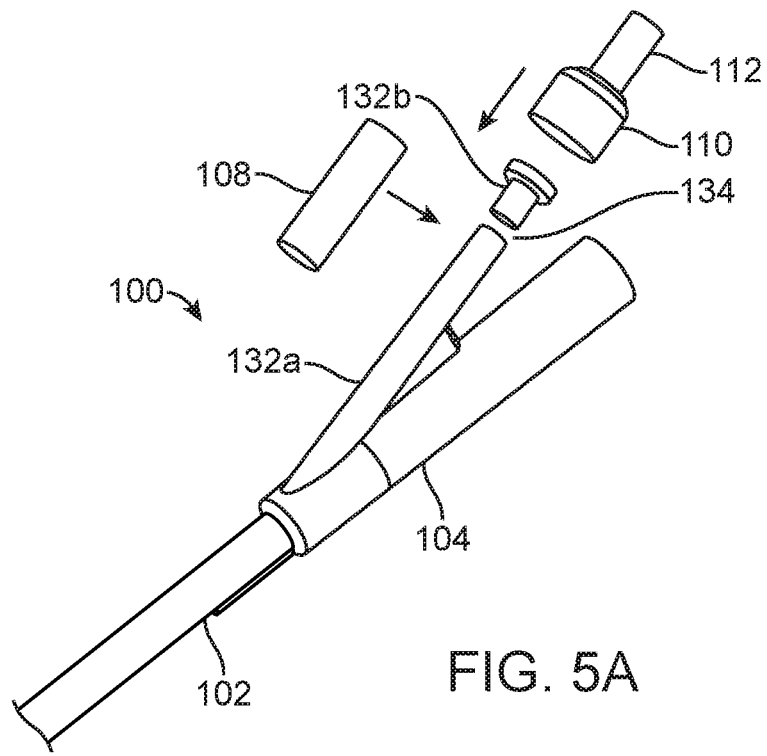
FIGS. 5A and 5B are perspective views of a proximal end of a urinary catheter, illustrating a method for assembling the proximal portion, according to an alternative embodiment.
Figure 5B:
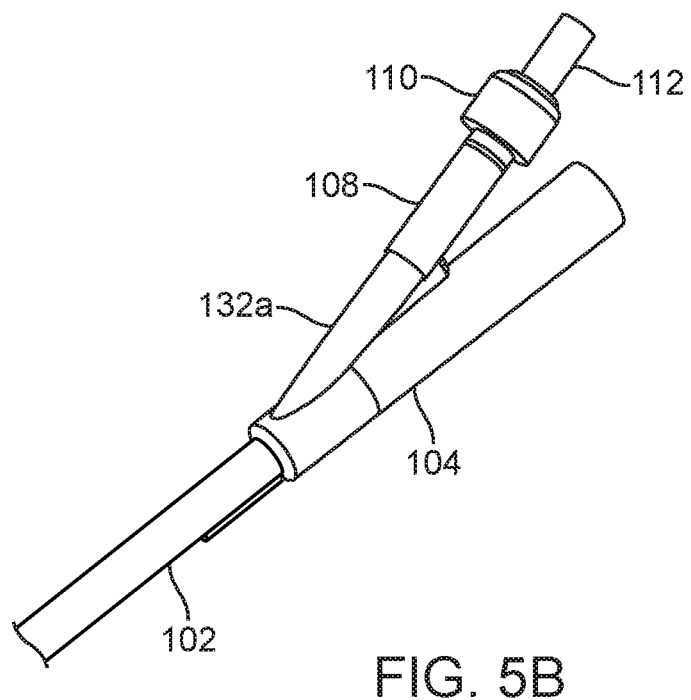

With reference now to FIGS. 5A and 5B, in an alternative embodiment, a second arm of connector 104 may be cut into two second arm portions 132a, 132b, leaving a gap 134 between the two. Pilot balloon 108 may be mounted over the two second arm portions 132a, 132b and gap 134, so that gap 134 acts as the aperture through which inflation fluid flows to fill pilot balloon 108. This embodiment may allow a simplified assembly process.

As illustrated in FIGS. 4A-5B and as described above, pilot balloon 108, in many embodiments, is shaped as a simple tube of material. Because a tube, like pilot balloon 108, can be extruded, a large number of tubes can be produced very inexpensively. The only processing required is cutting the tube to length. Unlike a simple tube, a conventional balloon must either be extruded and blown or dipped on a mandrel individually. Balloon blowing and dipping are both more expensive processes than extruding and cutting tubes. Therefore, one advantage of the method of manufacturing urinary catheter 100 is that the simple tubular shape of pilot balloon 108 and its assembly onto catheter 100 allow for very cost effective manufacturing. For example, some embodiments may have a manufacturing cost within approximately 10% of a cost of a conventional catheter with no safety features.

In various embodiments, a manufacturing method for making urinary catheter 100 may include any of the design modifications and features described above. For example, any of the different combinations of features, sizes, angles and/or wall thicknesses of pilot balloon 108, retention balloon 114, aperture 126 and/or retention balloon inflation hole 128 may be used, according to various alternative embodiments. Pilot balloon 108 and tube 106 may be glued onto connector 104 and check valve 112 in any suitable way and with any suitable amount of overlap. Similarly, retention balloon 114 may be glued or otherwise attached to catheter shaft 102 in any suitable way and with any suitable amount of overlap.

In one embodiment, a method for positioning urinary catheter 100 may first involve advancing distal tip 116 of urinary catheter 100 through the patient's urethra. Next, inflation fluid may be introduced into urinary catheter 100 via an inflation port on the end of check valve 112, to inflate retention balloon 114. In some embodiments, for example, about 5 cc to about 10 cc of the inflation fluid, such as sterile water, sterile saline or the like, may be injected using a syringe. The user may watch pilot balloon 108 during and/or after inflation. If the user observes pilot balloon 108 does not inflate, then he/she may assume retention balloon 114 has been safely inflated in the bladder.

If, on the other hand, pilot balloon 108 does inflate, even partially, the user may wait for at least a predefined amount of time to see if pilot balloon 108 deflates. This may be a beneficial step in the method, because sometimes pilot balloon 108 may partially or even completely inflate, even when retention balloon 114 is in the bladder. This may occur, for example, if the inflation fluid is injected into catheter 100 very quickly and/or with a great deal of force. If pilot balloon 108 deflates during the predefined amount of time, then the user may assume retention balloon 114 is safely inflated in the bladder and may leave the urinary catheter in place within the patient. If pilot balloon 108 does not deflate during the predefined amount of time, then the user may remove the inflation fluid from urinary catheter 100 (for example by pulling back the plunger on the inflation syringe) and either reposition or remove the urinary catheter from the patient. In various embodiments, the predefined amount of time may be any suitable amount of time, for example as short as three seconds, as long as thirty seconds or even a minute or more, and in one embodiment about ten seconds. In some embodiments, the method may also include visualizing at least the advancement of urinary catheter 100 via a radiographic imaging device and radiopaque strip 118 (or other radiopaque marker) on catheter 100.

Although various embodiments are described herein in detail, any of a number of modifications may be made to any given embodiment, without departing from the scope of the invention as it is defined by the following claims. Therefore, the description of embodiments herein is intended to be exemplary in nature and not limiting.

What is claimed is:

1. A urinary catheter for draining urine from a bladder of a patient, the urinary catheter comprising:
   an elongate, flexible, tubular catheter shaft having a proximal end and a distal end and consisting of silicone;
   a connector coupled with the proximal end of the catheter shaft, wherein the connector comprises:
      a first arm ending in a fluid outlet configured to allow urine to flow out of the urinary catheter; and
      a second arm comprising an aperture and ending in an inflation inlet used for introducing inflation fluid into the urinary catheter;
   a primary lumen extending through the catheter shaft from a fluid inlet at or near the distal end of the catheter shaft to the fluid outlet on the first arm of the connector;
   an inflation lumen extending through the catheter shaft from a distal filling hole in the catheter shaft to the inflation inlet on the second arm of the connector;
   a retention balloon mounted to the catheter shaft proximal to the fluid inlet and over the distal filling hole, wherein the retention balloon is made of silicone and comprises a preformed balloon shape when not inflated, a first wall thickness, and a first durometer; and
   a pilot balloon consisting of a tubular member mounted on the second arm of the connector over the aperture in a location that is outside the patient during use of the urinary catheter, wherein the pilot balloon is made of silicone and comprises a tubular shape when not inflated, a second wall thickness that is greater than the first wall thickness, and a second durometer that is greater than the first durometer;
   wherein the retention balloon is configured to inflate at a first inflation pressure, and the pilot balloon is configured to inflate at a second inflation pressure that is higher than the first inflation pressure and lower than a predetermined pressure threshold, wherein a difference between the first inflation pressure and the second inflation pressure is configured to allow the pilot balloon to deflate in 3-10 seconds if the first inflation pressure is below the predetermined threshold after the retention balloon is inflated, and wherein the pilot balloon will not deflate if the retention balloon pressure is above the predetermined threshold after filling.

2. The urinary catheter of claim 1, wherein the aperture in the second arm of the connector is selected from the group consisting of one hole, multiple holes, a slit, and a gap between two portions of the second arm.

3. The urinary catheter of claim 1, wherein a cross-sectional area of the aperture in the second arm of the connector is less than a cross-sectional area of the distal filling hole.

4. The urinary catheter of claim 1, further comprising a check valve attached to a proximal end of the second arm, wherein the inflation inlet comprises a proximal end of the check valve.

5. The urinary catheter of claim 1, wherein the retention balloon has a first length, and the pilot balloon has a second length that is different than the first length.

6. The urinary catheter of claim 1, wherein the retention balloon has a first radius, and the pilot balloon has a second radius that is less than the first radius.

7. The urinary catheter of claim 1, wherein the retention balloon has a first inflated shape, and the pilot balloon has a second inflated shape that is different than the first inflated shape.

8. The urinary catheter of claim 1, further comprising a radiopaque strip extending through at least a portion of the catheter shaft.

9. A method of manufacturing a urinary catheter for draining urine from a bladder of a patient, the method comprising:

providing an elongate, flexible, tubular catheter shaft having a proximal end and a distal end and consisting of silicone and further comprising:
  a primary lumen extending through the catheter shaft from a fluid inlet at or near the distal end of the catheter shaft to the proximal end of the catheter shaft; and
  an inflation lumen extending through the catheter shaft from a distal filling hole near the distal end of the catheter shaft to the proximal end of the catheter shaft;

attaching a connector with the proximal end of the catheter shaft, wherein the connector comprises:
  a first arm in fluid communication with the primary lumen and ending in a fluid outlet configured to allow urine to flow out of the urinary catheter; and
  a second arm comprising an aperture in fluid communication with the inflation lumen and ending in an inflation inlet used for introducing inflation fluid into the urinary catheter;

mounting a retention balloon on the catheter shaft over the distal filling hole and proximal to the fluid inlet, wherein the retention balloon is made of silicone, has a preformed balloon shape when not inflated, and has a first wall thickness and a first durometer; and mounting a tubular pilot balloon consisting of a tubular member on the second arm of the connector over the aperture in the second arm in a location that is outside the patient during use of the urinary catheter, wherein the pilot balloon is made of silicone and comprises a tubular shape when not inflated, a second wall thickness that is greater than the first wall thickness, and a second durometer that is greater than the first durometer, wherein the retention balloon is configured to inflate at a first inflation pressure, and the pilot balloon is configured to inflate at a second inflation pressure that is higher than the first inflation pressure and lower than a predetermined pressure threshold, wherein a difference between the first inflation pressure and the second inflation pressure is configured to allow the pilot balloon to deflate in 3-10 seconds if the first inflation pressure is below the predetermined threshold after the retention balloon is inflated, and wherein the pilot balloon will not deflate if the retention balloon pressure is above the predetermined threshold after filling.

10. The method of claim 9, further comprising forming the aperture in the second arm.

11. The method of claim 10, wherein forming the aperture comprises forming at least one of a hole, a slit or a cut in the second arm.

12. The method of claim 9, wherein a cross-sectional area of the aperture in the second arm is less than a cross-sectional area of the distal filling hole.

13. The method of claim 9, further comprising:
forming the tubular pilot balloon to have the tubular shape; and
forming the retention balloon to have the preformed balloon shape,
wherein a higher pressure is required to begin inflating the tubular pilot balloon than the retention balloon.

14. The method claim 9, further comprising:
forming the retention balloon to have the first balloon wall thickness; and
forming the pilot balloon to have the second balloon wall thickness.

15. The method of claim 9, further comprising:
forming the retention balloon to have a first length; and
forming the pilot balloon to have a second length that is different than the first length.

16. The method of claim 9, further comprising:
forming the retention balloon to have a first inflated shape; and
forming the pilot balloon to have a second inflated shape that is different than the first inflated shape.

* * * * *